US006955640B2

(12) United States Patent
Sanders et al.

(10) Patent No.: US 6,955,640 B2
(45) Date of Patent: Oct. 18, 2005

(54) BRACHYTHERAPY FOR ARRHYTHMIAS (75) Inventors: Richard S. Sanders, Woodbury, MN (US); Bruce H. Kenknight, Maple Grove, MN (US); David S. Wood, Temecula, CA (US); Richard V. Calfee, Houston, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 275 days.

(21) Appl. No.: 09/967,469

(22) Filed: Sep. 28, 2001

(65) Prior Publication Data
US 2003/0065240 A1 Apr. 3, 2003

(51) Int. Cl.⁷ ................................................ A61N 5/00
(52) U.S. Cl. ........................................................ 600/3
(58) Field of Search ............................... 600/1–8, 381, 600/518; 128/898; 604/530, 528, 103, 103.07; 606/15, 34, 41

(56) References Cited

U.S. PATENT DOCUMENTS

| 5,140,987 | A | * | 8/1992 | Schuger et al. ............. 600/381 |
| 5,713,828 | A | | 2/1998 | Coniglione .................... 600/7 |
| 5,807,395 | A | | 9/1998 | Mulier et al. ................. 606/41 |
| 5,814,028 | A | * | 9/1998 | Swartz et al. ............... 604/528 |
| 5,824,005 | A | * | 10/1998 | Motamedi et al. ............ 606/15 |
| 5,855,546 | A | * | 1/1999 | Hastings et al. ............... 600/3 |
| 5,863,284 | A | * | 1/1999 | Klein ............................. 600/3 |
| 5,868,680 | A | * | 2/1999 | Steiner et al. ............... 600/518 |
| 5,971,980 | A | | 10/1999 | Sherman ....................... 606/34 |
| 6,013,074 | A | * | 1/2000 | Taylor .......................... 606/34 |
| 6,063,078 | A | | 5/2000 | Wittkampf .................... 606/41 |
| 6,068,629 | A | * | 5/2000 | Haissaguerre et al. ......... 606/41 |
| 6,090,084 | A | * | 7/2000 | Hassett et al. ............... 604/530 |
| 6,152,920 | A | | 11/2000 | Thompson et al. ............ 606/41 |
| 6,161,543 | A | * | 12/2000 | Cox et al. .................... 128/898 |
| 6,179,833 | B1 | | 1/2001 | Taylor .......................... 606/34 |
| 6,196,963 | B1 | | 3/2001 | Williams ........................ 600/3 |
| 6,196,964 | B1 | | 3/2001 | Loffler et al. .................. 600/7 |
| 6,200,314 | B1 | | 3/2001 | Sherman ....................... 606/34 |
| 6,245,062 | B1 | | 6/2001 | Berube et al. ................. 606/33 |
| 6,283,910 | B1 | * | 9/2001 | Bradshaw et al. .............. 600/3 |
| 6,287,302 | B1 | | 9/2001 | Berube ......................... 606/33 |
| 6,296,603 | B1 | * | 10/2001 | Turnlund et al. ............... 600/3 |
| 6,308,093 | B1 | | 10/2001 | Armoundas et al. ......... 600/509 |
| 6,314,962 | B1 | | 11/2001 | Vaska et al. ................. 128/989 |
| 6,315,778 | B1 | | 11/2001 | Gambale et al. .............. 606/41 |
| 6,317,615 | B1 | | 11/2001 | KenKnight et al. .......... 600/372 |

FOREIGN PATENT DOCUMENTS

EP      1033147 A2    9/2000    ............ A61N/5/10

* cited by examiner

Primary Examiner—Eric F. Winakur
Assistant Examiner—Nikita R. Veniaminov
(74) Attorney, Agent, or Firm—Schwegman, Lundberg, Woessner & Kluth, P.A.

(57) ABSTRACT

An apparatus and method for brachytherapy. One method includes locating a region of cardiac tissue having a relatively large probability of originating or transmitting electrical signals which result in arrhythmic activity and irradiating the region of cardiac tissue to reduce the amount of arrhythmic activity. Irradiating can include regulating protein expression of myocardial cells, killing myocardial cells, ablating myocardial cells, irradiating sleeves of atrial muscle that extend from a left atrial wall around the pulmonary veins, and/or creating lesions that block electrical conduction through myocardial tissue. Locating the region can include locating a foci of an atrial arrhythmia or locating the foci adjacent a pulmonary vein.

84 Claims, 8 Drawing Sheets

BRACHYTHERAPY FOR ARRHYTHMIAS

TECHNICAL FIELD

The present invention relates generally to medical devices and medical procedures, and more particularly relates to an apparatus and method for treating cardiac arrhythmias.

BACKGROUND

During atrial fibrillation (AF) the two small upper chambers of the heart, the atria, quiver instead of beating effectively. AF often results in fast and irregular heartbeat, weakness of heart function, a high incidence of thromboembolic events, leading to stroke, and hemodynamic compromise. AF can also lead to tachycardia-induced cardiomyopathy.

One approach to treating AF uses radio-frequency catheter ablation to create lesions in a heart in an attempt to prevent AF and/or to control ventricular rate. A drawback to radio-frequency catheter ablation is that heat generated during the procedure may lead to excessive fibrosis of cardiac tissue or the pulmonary veins and/or to the formation of stroke-causing blood clots.

A need, therefore, exists for additional approaches to treating arrhythmias, including atrial fibrillation and other debilitating cardiac rhythms.

SUMMARY

The present system provides methods and apparatus for treating arrhythmias. One aspect provides a method which includes locating a region of cardiac tissue having a relatively large probability of originating or transmitting electrical signals which result in arrhythmic activity and irradiating the region of cardiac tissue to reduce the amount of arrhythmic activity. In one example, irradiating can include introducing a balloon having a predefined shape into a heart, inflating the balloon to position the balloon at least partially against or adjacent to the cardiac tissue of the heart, exposing the cardiac tissue adjacent the inflated balloon to a radioactive source so that the conductive pathways of the heart adjacent the inflated balloon are modified. In one example, irradiating can include introducing a catheter having a predefined shape into a heart, the catheter including a radioactive source, positioning the catheter at least partially against the region of cardiac tissue, exposing the cardiac tissue adjacent the catheter to the radioactive source, and modifying conductive pathways of the heart adjacent the catheter with radiation from the radioactive source.

One aspect of the present system provides a brachytherapy system for treating arrhythmias. In one embodiment, a brachytherapy system includes an elongate flexible catheter, an inflatable balloon coupled to the elongate flexible catheter, a pressurized gas source to inflate the balloon, and a wire having a radioactive source positioned on the wire, wherein the catheter receives and passes the wire to position the radioactive source adjacent a chamber of the inflatable balloon to allow nuclear energy to pass through a gas in the chamber of the balloon and irradiate tissue adjacent to the balloon.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Atrial fibrillation is one of the most common arrhythmias encountered by physicians. During atrial fibrillation the two small upper chambers of the heart, the atria, quiver instead of beating effectively. Symptoms of an atrial arrhythmia can include palpitations, but fatigue, dyspnea, and dizziness are not uncommon. Patients with an uncontrolled ventricular response during AF may occasionally develop a tachycardia-induced cardiomyopathy. In addition, because blood is not completely pumped from the atria, there is a chance that some blood might pool and clot. If a clot were to form and subsequently become lodged in an artery of the brain, a stroke results. About 15 percent of strokes occur in people with atrial fibrillation.

Because atrial fibrillation can lead to tachycardia-induced cardiomyopathy and/or stroke, atrial fibrillation is aggressively treated. There are two general approaches to treating atrial fibrillation. The first is with pharmacological therapy. The second is with nonpharmacological therapy.

With pharmacological therapy, medications are used in an attempt to restore and maintain sinus rhythm, provide rate control and/or to prevent thromboembolisms in patients AF. Medications such as digitalis, verapamil, diltiazem, and β-adrenergic blockers may be useful during AF to decrease the ventricular response that occurs over the atrioventricular (AV) node, but they rarely terminate AF. Rate control is most effective with intravenous verapamil, diltiazem, or β-blockers. To prevent thromboembolism, patients are often given aspirin and/or an additional anticoagulation, such as warfarin.

With nonpharmacological therapy, techniques such as surgery, endocardial radio-frequency catheter ablation and atrial pacing are used in an attempt to prevent AF and/or to control ventricular rate. The surgical approach to treating AF is based on the theory that large areas of the atria must be isolated electrically from each other to prevent AF. Endocardial radio-frequency catheter ablation can be used to create long linear lesions for this purpose. The maze procedure is another approach to treating AF. In the maze surgical operation, multiple atrial incisions are made to channel sinus impulses through a path, or "maze," to reach the AV node. This prevents a critical mass of contiguous atrial tissue from sustaining AF while maintaining atrial contractility. A substantial number of patients may require implantation of a permanent pacemaker after the maze procedure. Permanent pacing has also been attempted as a method to prevent AF.

The type of AF is also a consideration in determining a course of treatment. AF can either be chronic sustained AF or periodic (paroxysmal) AF. Paroxysmal AF refers to episodes of atrial fibrillation lasting, for example, minutes to hours for each episode. The heart rate reverts to normal in between these episodes. In chronic, sustained atrial fibrillation, the atria fibrillate all the time. Chronic, sustained AF is not difficult to diagnose. Doctors can hear the rapid and irregular heartbeats using a stethoscope. Abnormal heartbeats can also be felt by taking the patient's pulse. An electrocardiogram (EKG) is a brief recording of the heart's electrical rhythm. The irregular EKG tracings of atrial fibrillation are easy to recognize provided atrial fibrillation occurs during the EKG recording.

If episodes of atrial fibrillation occur intermittently, a standard EKG performed at the time of a doctor office visit may not detect this abnormal rhythm. Therefore, a Holter monitor (a continuous cassette recording of the heart rhythm for 24 hours) is often used to determine whether intermittent episodes of atrial fibrillation occur. If the fibrillating episodes are infrequent, a 24 hour Holter recording may not capture these sporadic episodes. In this situation, a patient-activated event recorder can be worn by the patient for 1 to 2 weeks. The patient presses a button to start the recording when he or she senses the onset of irregular heartbeats. These recordings are analyzed by the doctor at a later date.

Once atrial fibrillation is documented, attention is turned to determining the underlying cause(s) of the condition. Common causes of AF are coronary artery disease, mitral stenosis, mitral regurgitation, aortic stenosis, aortic regurgitation, hyperthyroidism, pulmonary embolism, COPD, pericarditis, myocarditis, cardiomyopathy, alcohol abuse, left atrial myxoma and pheochromocytoma. Another cause of AF is due to ectopic beats originating from the pulmonary veins. Ectopic beats from the pulmonary veins are known to initiate paroxysmal AF. It has been found that the origins of the atrial ectopic beats can occur 2 to 4 cm inside the veins. Thus, the pulmonary veins are an important source of ectopic beats, initiating frequent paroxysms of atrial fibrillation.

Brachytherapy is used to describe the use of radioactive isotopes in the treatment of cancer and benign diseases. An example includes the implantation of radioactive seeds into a cancerous prostate. In brachytherapy, sealed sources of radioactive material are used to deliver radiation at a very short distance by placing the sources within the tissues, cavities or lumens of a tumor. The physical benefit of this mode of treatment is that very high doses of radiation can be delivered directly or almost directly to neoplastic disease, in order to destroy the tissues of the tumor, with a very rapid fall off of dose to the surrounding normal tissues, in order to minimize side effects. In other words, brachytherapy is a site-specific method of treating disease by destroying the target tissue.

The present subject matter utilizes brachytherapy in treating cardiac arrhythmias. In one embodiment, brachytherapy is used to treat regions of cardiac tissue surrounding and/or within the pulmonary veins in an effort to prevent AF. By delivering localized doses of radiation, foci for AF located within and/or around the pulmonary veins are destroyed, thereby reducing the likelihood of AF originating from or being transmitted through this region of the heart. The present subject matter presents a detailed discussion of the treatment of cardiac tissue in and around the pulmonary veins for preventing AF. Other embodiments treat regions of the atrium and ventricle. Accordingly, the present subject matter is adaptable to provide treatment for preventing arrhythmias in any region of the cardiac tissue. These types of arrhythmias include, but are not limited to, atrial fibrillation, atrial flutter, atrial tachycardia, ventricular fibrillation, ventricular flutter and/or ventricular tachycardia.

Figure 1:
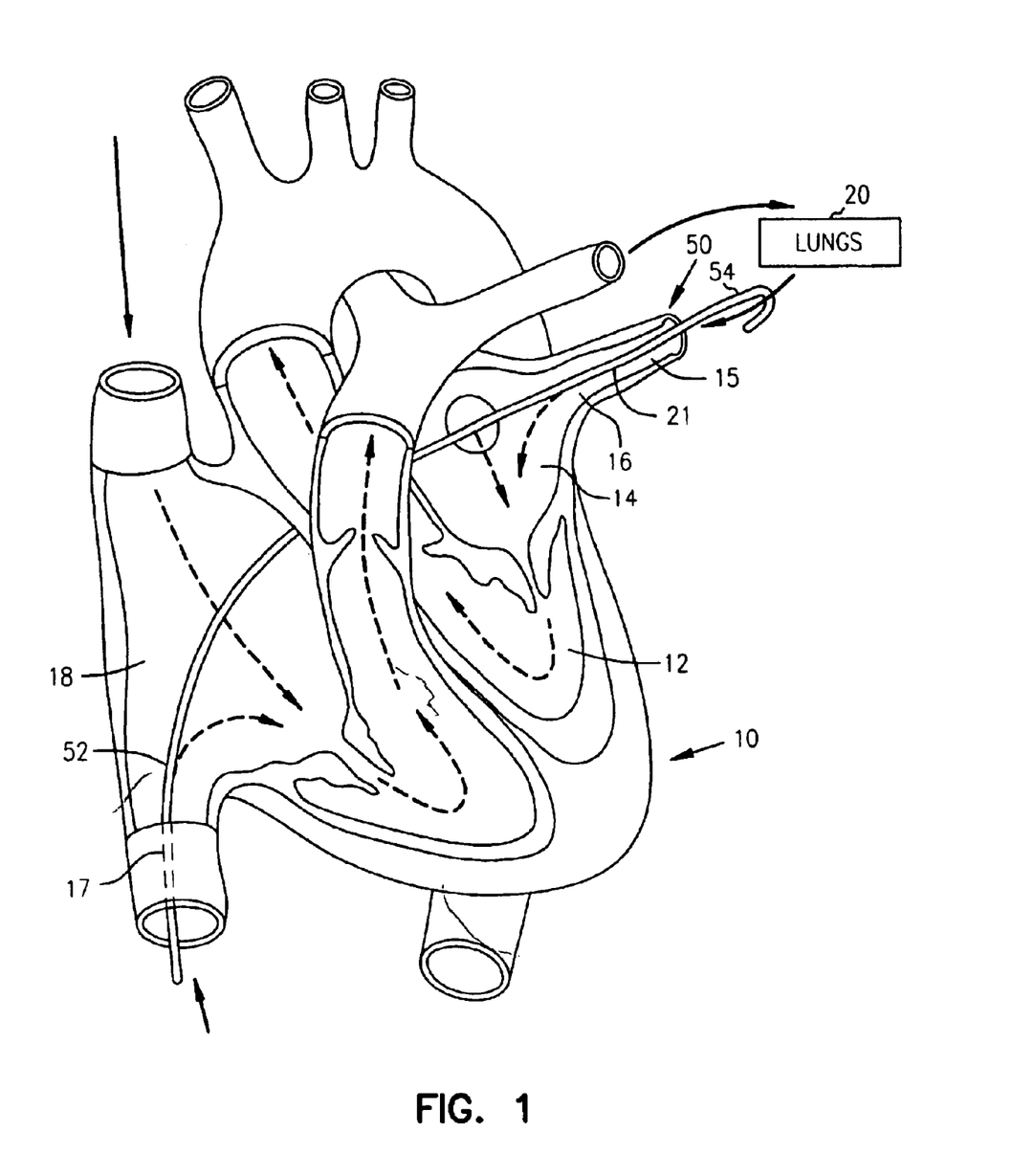
FIG. 1 shows a cut-away view of a heart and a schematic representation of an apparatus for treating arrhythmia implanted within the heart in accordance with one embodiment.

FIG. 1 shows a cut-away view of a heart 10 having an apparatus 50 according to one embodiment located therein. Heart 10 generally includes left ventricle 12, left atrium 14, inferior vena cava 17, right atrium 18, and pulmonary veins 15. Pulmonary veins 15 are shown entering the left atrium 14. The left atrium 14 receives oxygenated blood from the lungs 20 via the pulmonary veins 15. The pulmonary veins 15 enter the left atrium 14 and, while not having true valves at junction 16 of the veins 15 and the left atrium 14, sleeves of atrial muscle extend from the left atrial wall around the pulmonary veins 15 for approximately 1 to 4 centimeters and may exert a partial sphincter-like influence, tending to lessen reflux during atrial systole or mitral regurgitation.

Electrically isolating the sleeves of atrial muscle that extend into the pulmonary veins is believed to reduce and or eliminate ectopic beats that originate from the pulmonary veins. By electrically isolating this muscle tissue, a significant source of AF initiating ectopic beats will be eliminated. The present system provides a solution to treating arrhythmias by treating this cardiac condition through brachytherapy.

For example, apparatus 50 is a schematic representation of various example apparatuses which will be described in detail below. Apparatus 50 includes a catheter 52. The catheter is inserted through inferior vena cava 17 and the distal end 54 of the catheter is located proximate or within the pulmonary vein 15. A wire is inserted through a lumen of the catheter. A portion of the wire includes a radiation source 121. By locating radiation source 121 in a desired location, brachytherapy is applied to cardiac tissue proximate the radiation source. The tissue proximate radiation source 121 is irradiated. In one instance, the radiation modifies the conductive pathways within the tissue enough to reduce the amount of arrhythmatic activity of the tissue. In another example, the radiation prevents the conduction of action potentials arising from ectopic sources residing outside the irradiated area. In other words, the radiation either stops the electrical activity at its source or it blocks the electrical activity which arises elsewhere from traveling. Again, further examples and options regarding apparatus 50 and its implanted location will be discussed below.

Accordingly, one aspect of the present system provides a procedure which utilizes a technique of vascular brachytherapy to treat arrhythmias. During one example of the brachytherapy procedure, catheter 52 is used to guide radioactive source 121 to one or more cardiac locations so as to deliver therapeutic doses of radiation to the cardiac tissue. As noted above, these locations can include portions of the pulmonary veins, the left atrium, or left ventricle.

Figure 2:
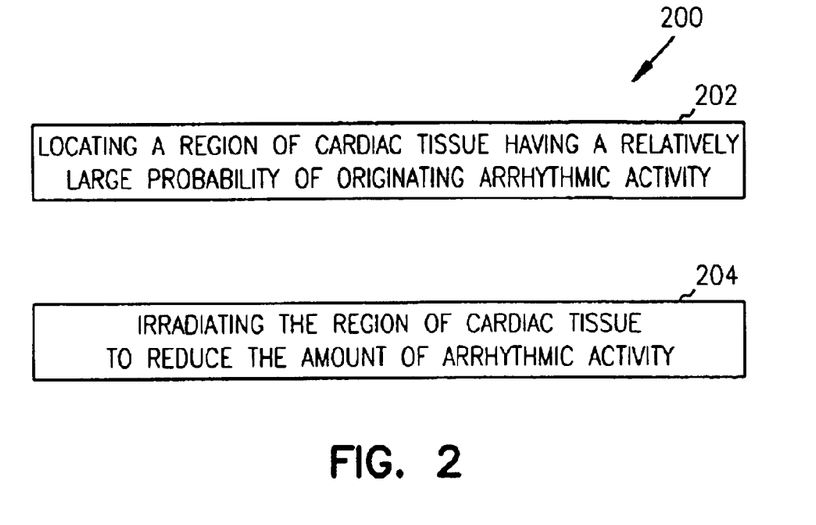
FIG. 2 is a flow chart of a method of treating arrhythmia according to one embodiment.

FIG. 2 shows a method 200 of treating arrhythmia according to one embodiment of the present system. At block 202, method 200 includes locating a region of cardiac tissue having a relatively large probability of originating or transmitting electrical signals which result in arrhythmic activity. At block 204, method 200 includes irradiating the region of cardiac tissue to reduce the amount of arrhythmic activity.

In one example of performing method 200, locating the region of cardiac tissue includes locating or identifying a supraventricular region having a relatively large probability of originating or transmitting electrical signals which result in an atrial arrhythmia. As detailed above, ectopic beats from the pulmonary veins are known to initiate paroxysmal AF. Accordingly, in some cases the supraventricular region which has a large probability of originating or transmitting electrical signals which result in an atrial arrhythmia is a supraventricular region which is adjacent a pulmonary vein or a supraventricular region which is at least partially within a pulmonary vein. In other examples of performing method 200, locating the region of cardiac tissue can include locating a ventricular region having a relatively large probability of originating or transmitting electrical signals which result in a ventricular arrhythmia. The ventricular arrhythmia can be ventricular fibrillation or tachycardia. One procedure to identify and locate the regions of interest is mapping the area using an electrophysiology (EP) diagnostic catheter.

In one example of method 200, the irradiating of block 204 is performed to change electrical conduction of the cardiac tissue identified in block 202. The electrical conduction of the cardiac tissue changes over time as the cardiac tissue in the region dies due to the irradiating. The radiation alters the genetic programs of the cells of the cardiac tissue. These genetic alterations cause the cell to die via changes in expression of critical proteins. This programmed cell death (apoptosis) within or proximate the pulmonary veins eliminates the ectopic activation foci and/or electrically uncouples or isolates the muscle sleeves that extend into the pulmonary veins from the left atrium.

In one embodiment, this process is accomplished by positioning a radiation source proximate the cardiac tissue for approximately 10 minutes. In other embodiments, the radiation source is positioned for a time anywhere in a range from 10 minutes to 90 minutes. Other examples vary the time depending on the location of and type of radiation source.

In one or more embodiments of the present method, irradiating regulates protein expression of myocardial cells in the cardiac tissue, irradiating kills myocardial cells in the cardiac tissue, and irradiating ablates myocardial cells in the cardiac tissue. In one example, irradiating the region of cardiac tissue includes creating lesions that block electrical conduction in the cardiac tissue. In one example, irradiating the region of cardiac tissue includes irradiating at least a portion of myocardial tissue that extends from a left atrial wall around the pulmonary veins to electrically isolate the myocardial tissue that surrounds the pulmonary veins. In one example, irradiating includes irradiating the region of cardiac tissue to form an elongate lesion in the cardiac tissue.

In one example, irradiating includes positioning a catheter having a radiation source therein in a position proximate the region of cardiac tissue having a large probability of originating or transmitting electrical signals which result in arrhythmic activity.

Figure 3A:
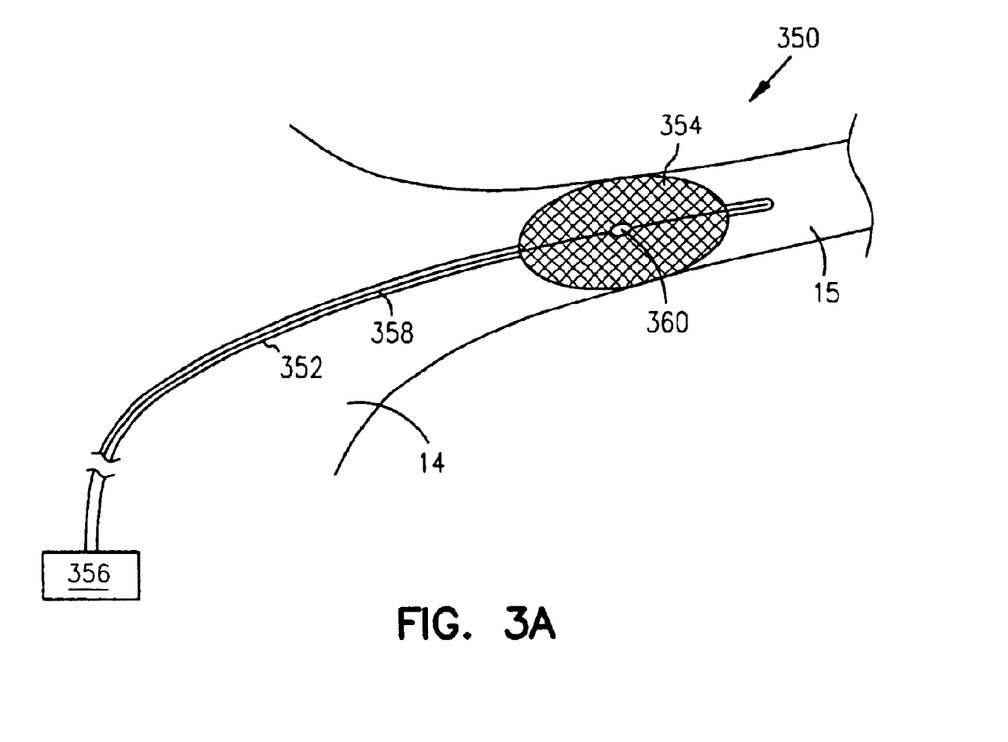
FIG. 3A shows a side view of an apparatus for treating arrhythmia according to one embodiment.

FIG. 3A shows a view of an brachytherapy apparatus 350 according to one embodiment. Brachytherapy apparatus 350 is shown as implanted in pulmonary vein 15 proximate left atrium 14. Brachytherapy apparatus 350 is one example of generic device 50 shown in FIG. 1.

Brachytherapy apparatus 350 includes an elongate flexible catheter 352, an inflatable balloon 354, a pressurized gas source 356, and a wire 358 having a radioactive source 360 positioned on the wire.

Figure 3B:
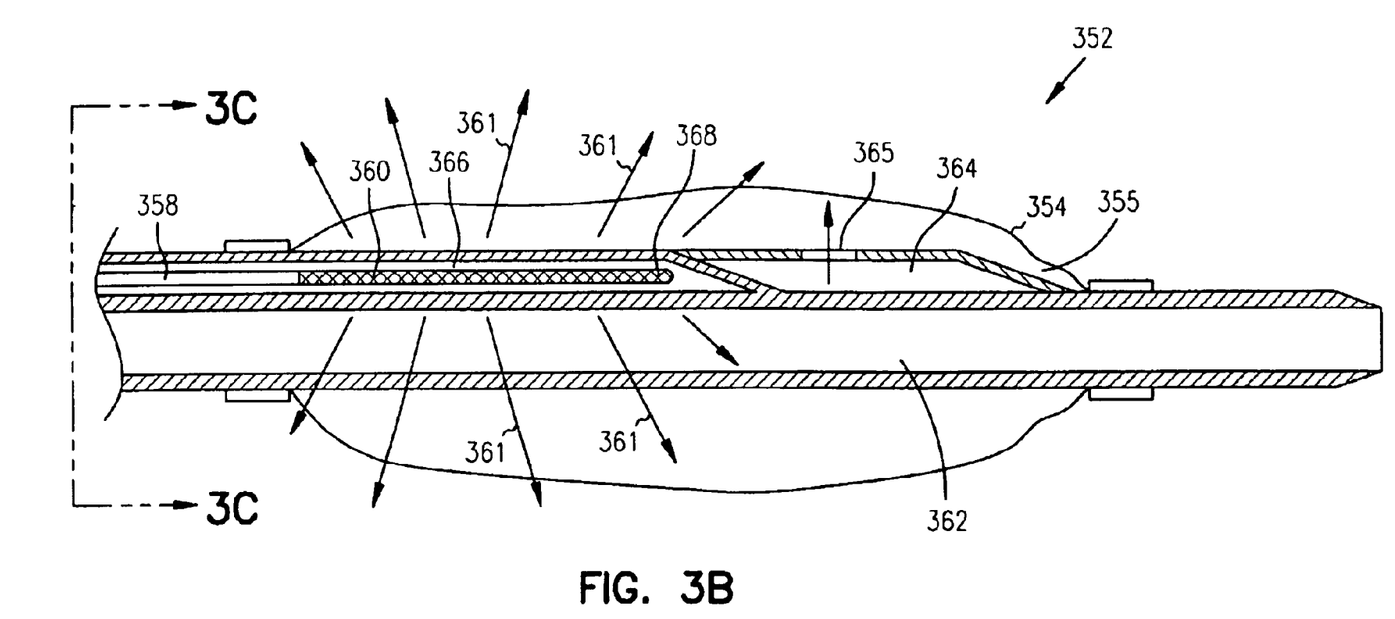
FIG. 3B shows a side sectional view of portions of the apparatus of FIG. 3A.
Figure 3C:
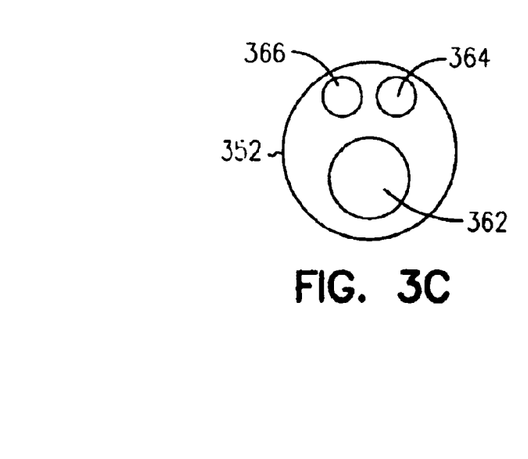
FIG. 3C shows a cross-section of the apparatus of FIG. 3B.

FIGS. 3B and 3C show one example of portions of the distal end of catheter 352. FIG. 3B shows a side sectional view of the distal end of the catheter and FIG. 3C shows a cross section of the catheter. In one embodiment, catheter 352 includes a first lumen 362 extending from a first inlet at the proximal end to first outlet 370 at the distal end, a second lumen 364 extending from a second inlet at the proximal end to a second outlet 365 positioned between the proximal and distal ends, and a third lumen 366 extending from a third inlet at the proximal end. The example catheter shown can be varied to omit one or more of these lumens or add other lumens for other purposes, as will be described below.

First lumen 362 provides a space for inserting a guidewire to guide and position catheter 352 to a desired location within the heart. Again, FIG. 1 shows one example location. Second lumen 364 is used for inflating balloon 354, as will be discussed below.

In this example, third lumen 366 is a centering lumen for holding wire 358 and radiation source 360. Third lumen 366 is located to approximately center wire 358 within the center of balloon 354 when the balloon is inflated. This provides for an even distribution of radiation 361 from radiation source 360 to the cardiac tissue located proximate thereto. In some embodiments, third lumen 366 can be located not within the center of the inflated balloon. Such a non-centered geometry can be used if the target tissue geometry requires such a placement, for example.

Inflatable balloon 354 is coupled to elongate flexible catheter 352. Inflatable balloon 354 at least partially encircles at least a portion of the elongate flexible catheter. Inflatable balloon 354 includes an interior surface that defines a chamber 355 in communication with outlet 365 of the second lumen 364. This allows a gas from gas source 356 (FIG. 3A) to be delivered to the balloon via second lumen 364 to inflate the balloon to secure the catheter within a desired location within the heart.

In one embodiment, pressurized gas source 356 is releasably coupled to an inlet of the second lumen 364. Pressurized gas source 356 inflates the balloon due to gas introduced into chamber 355 of the balloon. In one embodiment, the gas of pressurized gas source 356 is carbon dioxide gas. Among other advantages, using carbon dioxide provides that radiation 361 from radiation source 360 goes through the chamber of the balloon without appreciable attenuation. Moreover, carbon dioxide readily dissolves in blood should any inadvertent leakage occur. In some embodiments an inert gas is used to inflate balloon 354.

In one embodiment, inflatable balloon 354 has an inflated shape that is adapted to contact and conform with the cardiac tissue of a heart where the balloon is to be located. In some examples, the inflatable balloon has a predefined shape such that the balloon defines a geometry of a lesion created by the nuclear radiation. Accordingly, in various embodiment the inflated balloon shape is cylindrical, conical, spherical, spheroidal, or other pre-defined shape. In some examples, the balloon shape can be adapted to at least partially conform to a pulmonary vein. In some embodiments, the shape of the inflatable balloon is adapted to at least partially conform to a portion of a ventricular chamber or an atrial chamber. In one example, the inflatable balloon includes an exterior surface that defines one or more channels adapted to pass blood when the inflatable balloon is inflated. Other example shapes will be discussed below.

In one embodiment, wire 358 has radioactive source 360 positioned thereon so that the third lumen 366 receives and passes the wire to position the radioactive source 360 adjacent and within chamber 355 of the inflatable balloon to allow nuclear energy to pass through the gas in the chamber of the balloon and irradiate tissue in contact with the balloon. In one embodiment, radioactive source 360 is californium 252. Other isotopes which can be used include iridium 192, indium 114, cerium 144, ruthenium 106/rhodium 106 (during decay ruthenium 106 produces rhodium 106), strontium 90/yttrium 90 (during decay strontium 90 produces yttrium 90), phosphorous 32, ytterbium 169, and tungsten 188. Some embodiments include gold 198, iodine 125, palladium 103, samarium 145, cesium 131, cesium 137, cobalt 60, and selenium 75.

In one embodiment, wire 358 includes a distal tip 368 and radioactive source 360 is positioned on the wire at the distal tip of the wire. In other examples, the radioactive source is positioned along a predetermined portion of the wire.

Figure 3D:
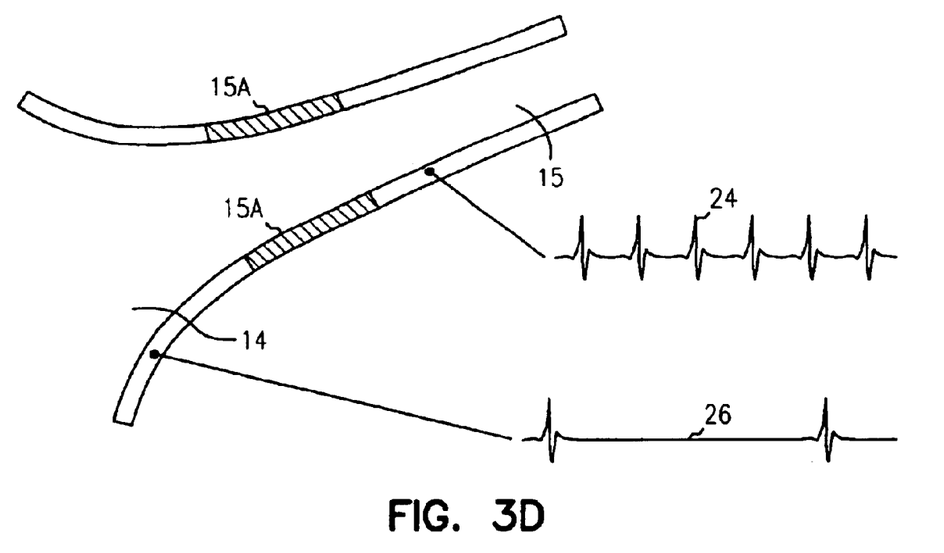
FIG. 3D shows an example of lesions within the heart produced by the apparatus of FIG. 3A.

FIG. 3D shows a schematic representation of portions of pulmonary veins 15 showing lesions 15A thereon after removal of the radiation source from the heart. Also shown are example EKGs 24 and 26 of the pulmonary vein region 15 and atrial region 14, respectively, once lesions 15A have stopped the electrical conduction from the pulmonary veins to the atrium. As can be seen, the present technique blocks the conduction of the electrical signals. Lesions 15A have a shape and size determined by the shape of the implanted balloons and the length of time the radiation source is left within the balloon. The shape of the balloon can help determine the size of the lesions since the area of tissue that receives the majority of the radiation through the balloon is the tissue in contact with the outer balloon surface. Accordingly, using a given radiation source, a long, skinny balloon will develop long lesions and a short, stout balloon will develop shorter lesions. The portion of the outer surface of the balloon which is not in contact with the tissue acts as a mask.

Figure 4:
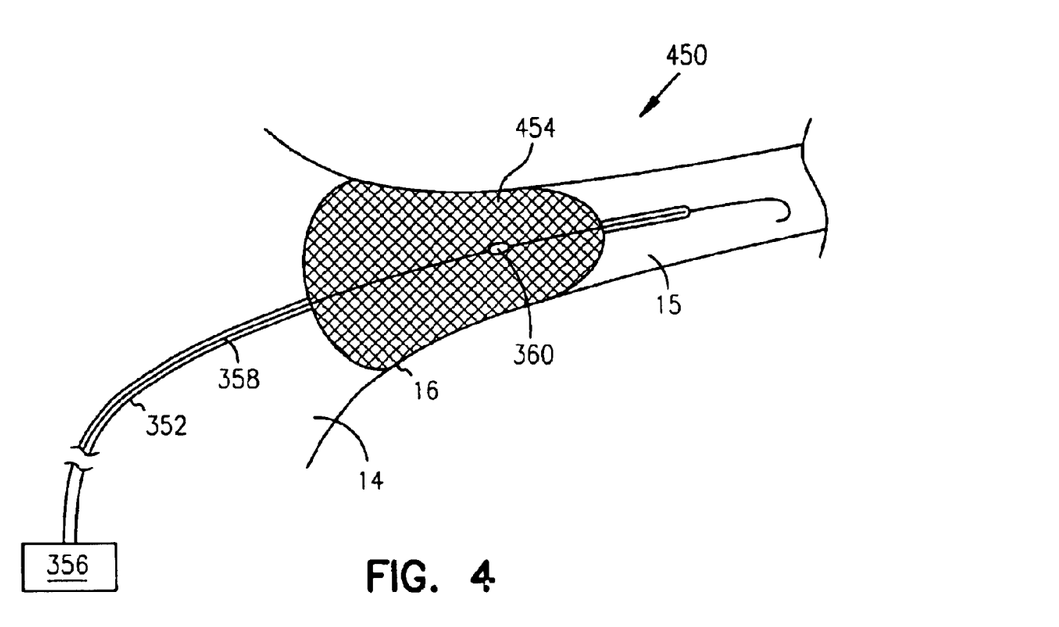
FIG. 4 shows a view of an apparatus for treating arrhythmia according to one embodiment.

FIG. 4 shows one embodiment of a brachytherapy apparatus 450 according to one embodiment. Brachytherapy apparatus 450 shares some features of brachytherapy apparatus 350 and like items have like numbers and will not be described in detail.

Brachytherapy apparatus 450 includes an elongate flexible catheter 352, an inflatable balloon 454, a pressurized gas source 356, and a wire 358 having a radioactive source 360 positioned on the wire.

In this example, inflatable balloon 454 has an inflated shape which is adapted to wedge within the junction region 16 between left atrium 14 and pulmonary vein 15. Since the region of tissue which receives the radiation is the region in contact with the outer surface of the balloon, this shape provides a lesion which lies along a portion of the left atrium and runs within pulmonary vein 15. Accordingly, in this example, the shape of the inflatable balloon is adapted to at least partially conform to a portion of an atrial chamber.

Figure 5:
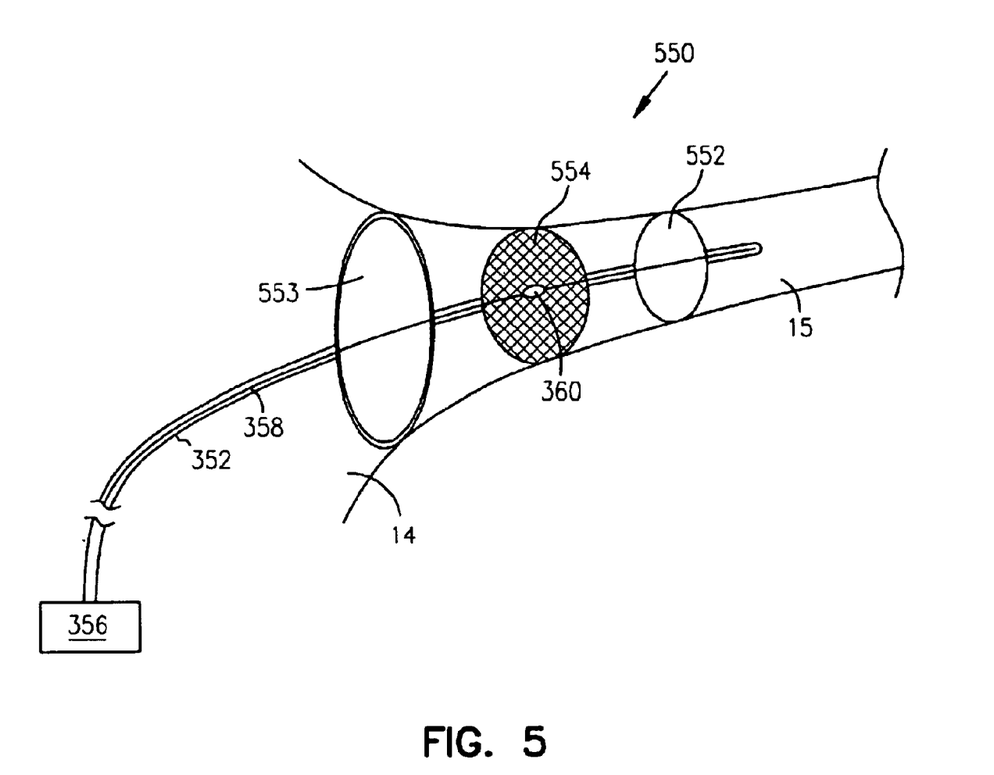
FIG. 5 shows a view of an apparatus for treating arrhythmia according to one embodiment.

FIG. 5 shows a brachytherapy apparatus 550 according to one embodiment. Brachytherapy apparatus 550 shares some features of brachytherapy apparatus 350 and like items have like numbers and will not be described in detail.

Brachytherapy apparatus 550 includes elongate flexible catheter 352, a first inflatable balloon 552, a second inflatable balloon 553 and a third inflatable balloon 554, a pressurized gas source 356, and a wire 358 having a radioactive source 360 positioned on the wire and located within inflatable balloon 554.

Inflatable balloons 552–554 are adapted to position the radiation source 360 within a portion of the pulmonary vein 15. In this example, outer balloons 552 and 553 help to balance wire 358 to keep the wire centered within the pulmonary vein. This keeps the radiation level relatively uniform all around the radiation source.

Catheter 352 can include a separate lumen for inflating each of balloons 552-554. This allows the orientation of wire 358 and radiation source 360 to be precisely controlled by the operator controlling the inflation of the balloons. In one example, two or more of the balloons 552–554 have inlets which are coupled to the same lumen and thus the balloons are inflatable at the same pressure and rate.

Figure 6:
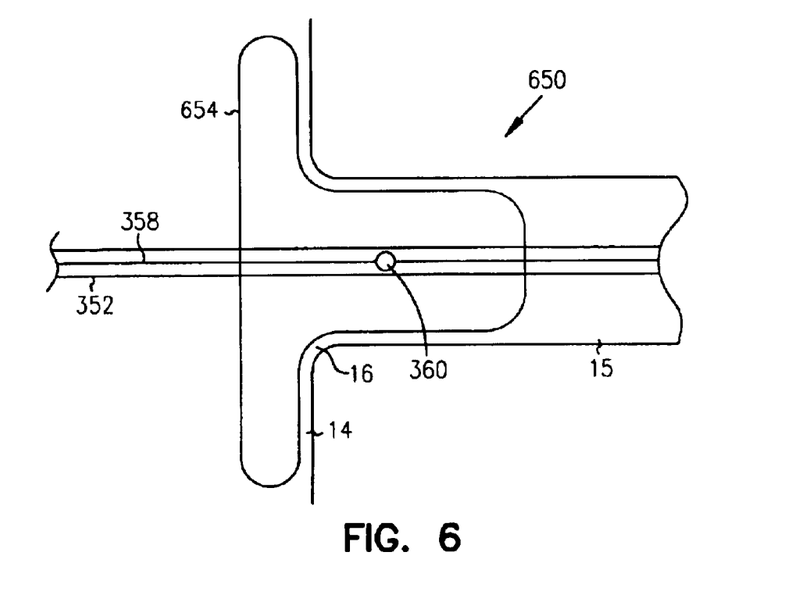
FIG. 6 shows a view of an apparatus for treating arrhythmia according to one embodiment.

FIG. 6 shows one embodiment of a brachytherapy apparatus 650 according to one embodiment. Brachytherapy apparatus 650 shares some features of brachytherapy apparatus 350 and like items have like numbers and will not be described in detail.

Brachytherapy apparatus 650 includes an elongate flexible catheter 352, an inflatable balloon 654, and a wire 358 having a radioactive source 360 positioned on the wire.

Inflatable balloon 654 includes a "champagne cork" shape and is adapted to wedge within the junction region 16 between left atrium 14 and pulmonary vein 15. This shape provides a lesion which lies along a portion of the left atrium and runs within pulmonary vein 15. Accordingly, in this example, the shape of the inflatable balloon is adapted to at least partially conform to a portion of an atrial chamber.

Figure 7:
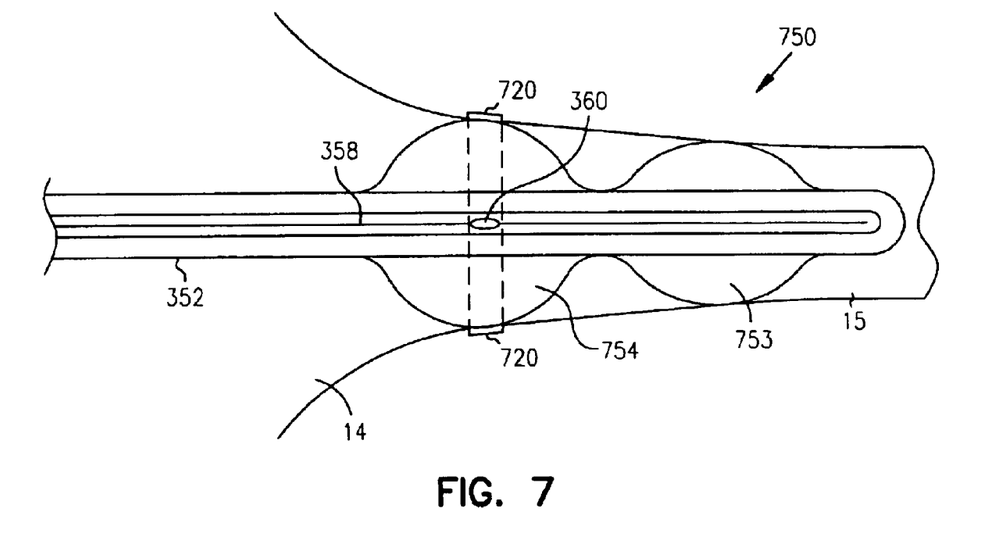
FIG. 7 shows a view of an apparatus for treating arrhythmia according to one embodiment.

FIG. 7 shows a brachytherapy apparatus 750 according to one embodiment. Brachytherapy apparatus 750 shares some features of brachytherapy apparatus 350 and like items have like numbers and will not be described in detail.

Brachytherapy apparatus 750 includes elongate flexible catheter 352, a first inflatable balloon 753, a second inflatable balloon 754, and a wire 358 having a radioactive source 360 positioned on the wire and located within inflatable balloon 754.

Inflatable balloons 753–754 are adapted to position the radiation source 360 within a portion of the pulmonary vein 15. In this example, balloon 753 is an alignment balloon for balancing and aligning radiation source 360 within the vein. This keeps the radiation level relatively constant all around the radiation source. Balloon 754 is shaped to provide lesions 720 within pulmonary vein 15

Catheter 352 can include a separate lumen for inflating each of balloons 753–754. This allows the orientation of wire 358 and radiation source 360 to be precisely controlled by the operator controlling the inflation of the balloons. In one example, balloons 753 and 754 have inlets which are coupled to the same lumen and thus the balloons are inflatable at the same pressure and rate.

Figure 8:
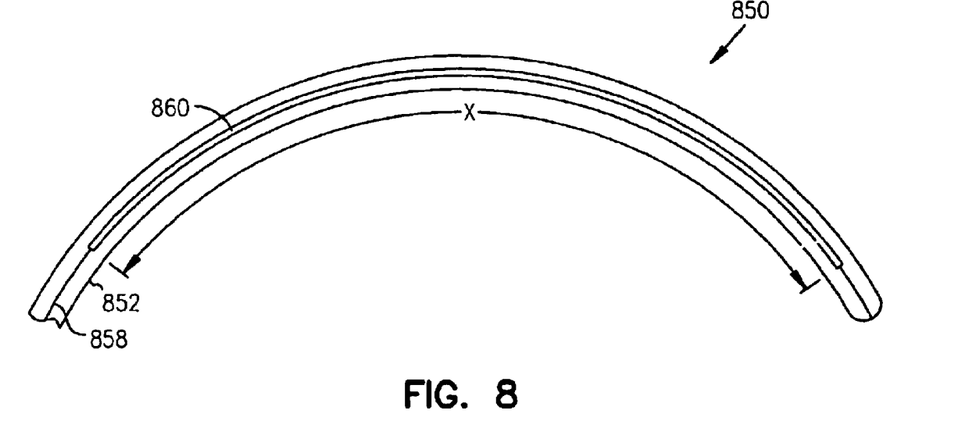
FIG. 8 shows a view of an apparatus for treating arrhythmia according to one embodiment.

FIG. 8 shows a brachytherapy apparatus 850 according to one embodiment. Brachytherapy apparatus 850 includes an elongate flexible catheter 852 and a wire 858 having a radioactive source 860 positioned on the wire. The wire 858 is located within a lumen of the catheter. In this embodiment, catheter 852 is a steerable, pre-shaped linear catheter. In this example, radioactive source 860 has a length of approximately 2.0 cm. Other embodiments can range from approximately 0.5 cm to approximately 4.0 cm. In this example, a balloon is not used. Instead, catheter 852 is steered into position using a guide catheter, for example. The catheter 852 is pre-shaped so that it is positionable in a desired location within the heart. For example, catheter 852 can be positioned so that radiation source 860 is centered within a portion of the pulmonary vein (See FIG. 1). In one embodiment, the predefined shape of catheter 852 is adapted to conform to a wall of a cardiac chamber.

Figure 9:
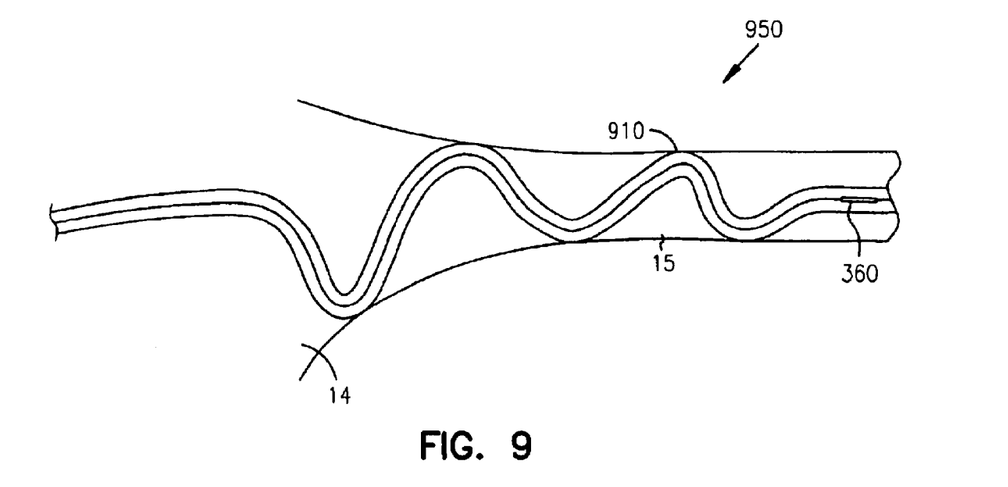
FIG. 9 shows a view of an apparatus for treating arrhythmia according to one embodiment.

FIG. 9 shows a brachytherapy apparatus 950 according to one embodiment. Brachytherapy apparatus 950 includes a helical-shaped catheter 910 having a source material 960 positioned within the catheter. In this example, helical-shaped catheter 910 includes a shape designed to fit within the pulmonary veins 15. Radiation source 360 can be located along various portions within catheter 910 to allow a user to treat a pre-determined portion of cardiac tissue.

Figure 10:
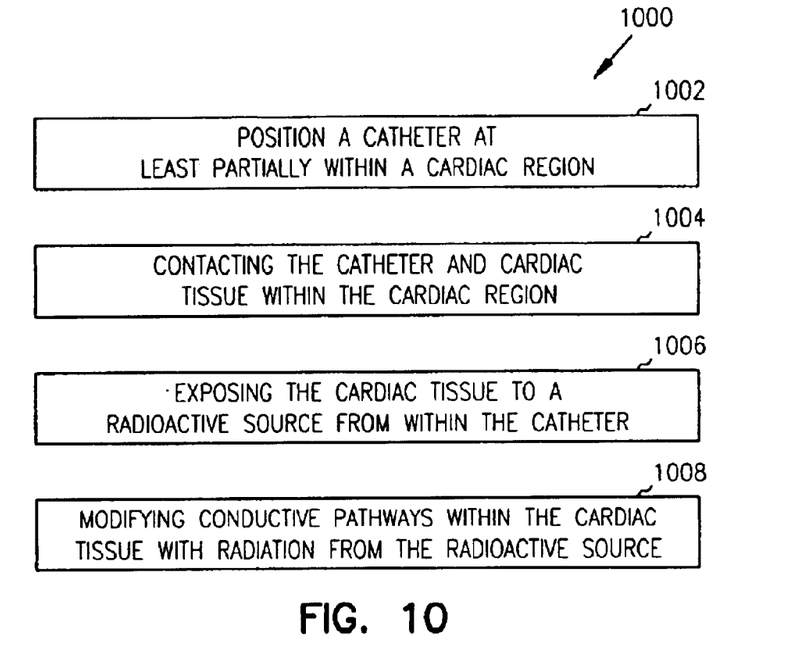
FIG. 10 is a flow chart of a method of treating arrhythmia according to one embodiment.

FIG. 10 shows a flowchart of a method 1000 according to one embodiment. Method 1000 can be performed using one or more features of the brachytherapy apparatuses described above. Method 1000 includes positioning a catheter having a balloon at least partially within a cardiac region (1002), inflating the balloon, where at least a portion of the balloon contacts cardiac tissue within the cardiac region (1004), exposing the cardiac tissue to a radioactive source through the inflated balloon (1006), and modifying conductive pathways within the cardiac tissue with radiation from the radioactive source (1008). In some embodiments, the catheter is positioned at least partially within the supraventricular region.

In one example, modifying conductive pathways of the heart includes creating a lesion having a geometry defined by a predefined shape of the balloon. The lesion geometry can be controlled through selecting the shape of balloon. Other geometries include the shapes and structures described above in FIG. 3A–FIG. 7. In some embodiments, the method can include selecting a shape of the balloon to conform to the one or more atrial arrhythmia foci identified in the supraventricular region. The balloon shape can be selected based on the identified arrhythmia foci. In another example, the radioactive source can be moved within the balloon to create an elongate lesion. In one example of the present method, the balloon is inflated with a gas such as a carbon dioxide gas. Other methods include an inert gas.

In one example, exposing the cardiac tissue adjacent the inflated balloon to the radioactive source includes introducing a wire through the inflated balloon, where the wire includes the radioactive source. In one example, exposing the cardiac tissue includes positioning the radioactive source within the inflated balloon so as to expose tissue adjacent the inflated balloon to a uniform level of nuclear radiation.

Exposing the cardiac tissue to a radiation source can include exposing at least a portion of myocardial tissue that extends from a left atrial wall around the pulmonary veins to electrically isolate the myocardial tissue that surrounds the pulmonary veins. In various embodiments, the exposure time can range from approximately 10 minutes to approximately 90 minutes.

In one example, the method can further include identifying one or more atrial arrhythmia foci in the supraventricular region before positioning the balloon. This can include identifying a foci adjacent a pulmonary vein. The inflated balloon is then positioned so that at least a portion of the balloon contacts endocardial tissue adjacent the one or more identified atrial arrhythmia foci. The operator then exposes the endocardial tissue adjacent the one or more identified atrial arrhythmia foci to the radioactive source through the inflated balloon.

Figure 11:
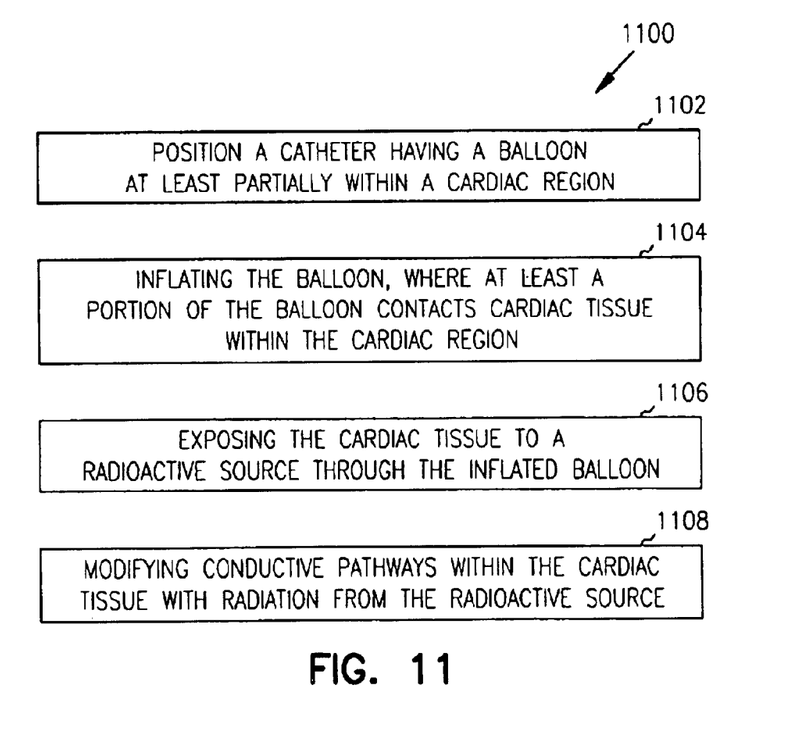
FIG. 11 is a flow chart of a method of treating arrhythmia according to one embodiment.

FIG. 11 shows a flowchart representing a method 1100 for performing brachytherapy according to one embodiment. Method 1100 includes positioning a catheter at least partially within a cardiac region (1102), contacting the catheter and the cardiac tissue within the region (1104), exposing the cardiac tissue to a radioactive source from within the catheter (1106), and modifying the conductive pathways within the cardiac tissue with radiation from the radioactive source (1108).

In one example, method 1100 includes introducing a catheter having a predefined shape into the cardiac region of the heart. One example is shown above and discussed regarding FIG. 8. Another example is shown and discussed regarding FIG. 9.

Certain features of method 1100 are similar to the methods and systems described above and will be omitted for sake of brevity. By way of example, but not meant to be limiting or exhaustive, method 1100 can include positioning the catheter at least partially within a supraventricular region; identifying one or more atrial arrhythmia foci in the supraventricular region; identifying a foci adjacent a pulmonary vein; exposing at least a portion of myocardial tissue that extends from a left atrial wall around the pulmonary veins to electrically isolate the myocardial tissue that surrounds the pulmonary veins; positioning the catheter at least partially within a ventricular region; moving the radioactive source within the catheter so as to create an elongate lesion.

Among other advantages, the system and apparatuses described herein do not use thermal means to kill tissue. Thermal heat can cause blood clots. Moreover, the present system does not use radio-frequency to kill tissue. This technique also produces heat and can result in cavitation of the blood. These thermal and RF techniques can also result in stenosis of the tissue surrounding the element. In contrast, the present brachytherapy system modifies the electrical conduction of the cardiac tissue over time as the cardiac tissue in the region dies due to the irradiating. As discussed above, the radiation alters the genetic programs of the cells of the cardiac tissue. These genetic alterations cause the cell to die via changes in expression of critical proteins. This programmed cell death within or proximate the pulmonary veins eliminates the ectopic activation foci and/or electrically uncouples or isolates the muscle sleeves that extend into the pulmonary veins from the left atrium. Accordingly, the present system provides an advantage in that using brachytherapy for treating cardiac arrhythmias is a simple, safe, and cost-effective means of addressing and preventing arrhythmias.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method comprising:
locating a region of cardiac tissue having a relatively large probability of originating or transmitting electrical signals which result in arrhythmic activity; and
irradiating the region of cardiac tissue with a radioactive source to reduce the amount of arrhythmic activity.

2. The method of claim 1, wherein the irradiating is performed to change electrical conduction of the cardiac tissue.

3. The method of claim 2, wherein electrical conduction and spontaneous depolarization of the cardiac tissue changes over time as the cardiac tissue in the region becomes electrically inactive due to irradiation.

4. The method of claim 2, wherein irradiating includes regulates protein expression of myocardial cells in the cardiac tissue.

5. The method of claim 2, wherein irradiating includes genetically programming a death of myocardial cells in the cardiac tissue.

6. The method of claim 2, wherein irradiating includes providing frank necrosis of myocardial cells in the cardiac tissue.

7. The method of claim 1, wherein irradiating the region of cardiac tissue includes creating lesions that block electrical conduction in the cardiac tissue.

8. The method of claim 1, wherein locating the region of cardiac tissue includes locating a supraventricular region having a relatively large probability of triggering and contributing to the maintenance of an atrial arrhythmia.

9. The method of claim 8, wherein the supraventricular region is adjacent a pulmonary vein.

10. The method of claim 8, wherein the supraventricular region is at least partially in a pulmonary vein.

11. The method of claim 8, wherein irradiating the region of cardiac tissue includes irradiating at least a portion of myocardial tissue that extends from a left atrial wall around the pulmonary veins to electrically isolate the myocardial tissue that surrounds the pulmonary veins.

12. The method of claim 1, wherein locating the region of cardiac tissue includes locating a ventricular region having a relatively large probability of originating or transmitting electrical signals which result in a ventricular arrhythmia.

13. The method of claim 12, wherein the ventricular arrhythmia is a ventricular tachycardia or fibrillation.

14. The method of claim 1, wherein irradiating the region of cardiac tissue includes irradiating the region of cardiac tissue to form an elongate lesion in the cardiac tissue.

15. A method comprising:
locating a region of cardiac tissue having a relatively large probability originating or transmitting electrical signals which result in arrhythmic activity; and
irradiating the region of cardiac tissue with a radioactive source to reduce the amount of
arrhythmic activity, wherein irradiating includes:
introducing a balloon having a predefined shape into a heart;
inflating the balloon having the predefined shape to position the balloon a least partially against the cardiac tissue of the heart;
exposing the cardiac tissue adjacent the inflated balloon to a radioactive source; and
modifying conductive pathways of the heart adjacent the inflated balloon with radiation from the radioactive source.

16. The method of claim 15, wherein exposing the cardiac tissue includes locating the radioactive source within the inflated balloon so as to expose tissue adjacent the inflated balloon to a uniform level of radiation.

17. The method of claim 15, wherein modifying the conductive pathways of the heart includes creating a lesion having a geometry defined by the predefined shape of the balloon.

18. The method of claim 17, wherein creating the lesion includes controlling a lesion geometry through selecting the shape of balloon.

19. The method of claim 15, wherein the inflated balloon has an elongate body, and exposing the cardiac tissue includes moving the radioactive source within the elongate body of the balloon so as to create an elongate lesion.

20. The method of claim 15, wherein the inflated balloon has a cylindrical body.

21. The method of claim 15, wherein exposing the cardiac tissue adjacent the inflated balloon to the radioactive source includes introducing a wire through the inflated balloon, where the wire includes the radioactive source.

22. The method of claim 15, wherein inflating the balloon includes inflating the balloon with a gas.

23. The method of claim 22, wherein the gas is carbon dioxide gas.

24. A method comprising:
locating a region of cardiac tissue having a relatively large probability of originating or transmitting electrical signals which result in arrhythmic activity; and
irradiating the region of cardiac tissue with a radioactive source to reduce the amount of arrhythmic activity, wherein irradiating includes:
introducing a catheter having a predefined shape into a heart, the catheter including a radioactive source;
positioning the catheter at least partially against the region of cardiac tissue;
exposing the cardiac tissue adjacent the catheter to the radioactive source; and
modifying conductive pathways of the heart adjacent the catheter with radiation from the radioactive source.

25. The method of claim 24, wherein locating includes mapping the heart using an electrophysiology (EP) diagnostic catheter.

26. A method of preventing arrhythmia, the method comprising:
positioning a catheter having a balloon at least partially within a cardiac region;
inflating the balloon, where at least a portion of the balloon contacts cardiac tissue within the cardiac region;
exposing the cardiac tissue to a radioactive source through the inflated balloon; and
modifying conductive pathways within the cardiac tissue with radiation from the radioactive source so that the cardiac tissue which is modified cannot originate or transmit electrical signals which result in arrhythmic activity.

27. The method of claim 26, wherein positioning the catheter includes positioning the catheter at least partially within a supraventricular region.

28. The method of claim 26, including identifying a supraventricular region of cardiac tissue having a relatively large probability of originating or transmitting electrical signals which result in arrhythmic activity;
inflating the balloon, where at least a portion of the balloon contacts endocardial tissue adjacent the supraventricular region of cardiac tissue; and exposing the endocardial tissue adjacent the supraventricular region of cardiac tissue to the radioactive source through the inflated balloon.

29. The method of claim 28, including selecting a shape of the balloon to conform to the identified supraventricular region of cardiac tissue.

30. The method of claim 28, wherein identifying a supraventricular region of cardiac tissue includes identifying a region within or adjacent a pulmonary vein.

31. The method of claim 30, wherein exposing the endocardial tissue adjacent the supraventricular region of cardiac tissue to the radioactive source includes exposing at least a portion of myocardial tissue that extends from a left atrial wall around the pulmonary veins to electrically isolate the myocardial tissue that surrounds the pulmonary veins.

32. The method of claim 28, further including selecting a predefined shape of the balloon based on the identified supraventricular region.

33. The method of claim 28, wherein identifying a supraventricular region of cardiac tissue includes mapping a heart using an electrophysiology (EP) diagnostic catheter.

34. The method of claim 26, wherein destroying conductive pathways of the heart includes creating a lesion having a geometry defined by a predefined shape of the balloon.

35. The method of claim 34, wherein creating the lesion includes controlling a lesion geometry through selecting the shape of the balloon.

36. The method of claim 26, wherein positioning the catheter includes positioning the catheter at least partially within a ventricular region.

37. The method of claim 26, wherein exposing the endocardium includes locating the radioactive source within the inflated balloon so as to expose cardiac tissue adjacent the inflated balloon to a uniform level of radiation.

38. The method of claim 26, wherein the inflated balloon has an elongate body, and exposing the cardiac tissue includes moving the radioactive source within the elongate body of the balloon so as to create an elongate lesion.

39. The method of claim 26, wherein the inflated balloon has a cylindrical body.

40. The method of claim 26, wherein exposing the endocardium adjacent the inflated balloon to the radioactive source includes introducing a wire through the inflated balloon, where the wire includes the radioactive source.

41. The method of claim 26, wherein inflating the balloon includes inflating the balloon with a gas.

42. The method of claim 41, wherein the gas is carbon dioxide gas.

43. A method of preventing arrhythmia, the method comprising:
positioning a catheter at least partially within a cardiac region and proximate a cardiac tissue;
exposing the cardiac tissue to a radioactive source from within the catheter; and
modifying conductive pathways within the cardiac tissue with radiation from the radioactive source so that the cardiac tissue which is modified cannot originate or transmit electrical signals which result in arrhythmic activity.

44. The method of claim 43, wherein positioning the catheter includes positioning the catheter at least partially within a supraventricular region.

45. The method of claim 43, wherein the method further includes identifying a supraventricular region of cardiac tissue having a relatively large probability of originating or transmitting electrical signals which result in arrhythmic activity; and contacting the catheter and the cardiac tissue proximate the identified supraventricular region.

46. The method of claim 45, wherein identifying a supraventricular region includes identifying a region adjacent or within a pulmonary vein.

47. The method of claim 46, wherein exposing the cardiac tissue includes exposing at least a portion of myocardial tissue that extends from a left atrial wall around the pulmonary veins to electrically isolate the myocardial tissue within or surrounding the pulmonary veins.

48. The method of claim 43, wherein positioning the catheter includes positioning the catheter at least partially within a ventricular region.

49. The method of claim 43, wherein exposing the cardiac tissue includes moving the radioactive source within the catheter so as to create an elongate lesion.

50. The method of claim 43, wherein exposing the cardiac tissue to the radioactive source includes introducing a wire through the catheter, where the wire includes the radioactive source.

51. A method of preventing arrhythmia, the method comprising:
locating a region of cardiac tissue having a relatively large probability of originating or transmitting electrical signals which result in arrhythmic activity; and
irradiating the region of cardiac tissue with a radioactive source to modify electrical conduction of the cardiac tissue so that the cardiac tissue which is modified cannot originate or transmit electrical signals which result in arrhythmic activity.

52. The method of claim 51, wherein electrical conduction and spontaneous depolarization of the cardiac tissue changes over time as the cardiac tissue in the region becomes electrically inactive due to irradiation.

53. The method of claim 51, wherein irradiating includes regulating protein expression of myocardial cells in the cardiac tissue.

54. The method of claim 51, wherein irradiating includes genetically programmed a death of myocardial cells in the cardiac tissue.

55. The method of claim 51, wherein irradiating includes providing frank necrosis of myocardial cells in the cardiac tissue.

56. A method of preventing arrhythmia, the method comprising:
locating a region of cardiac tissue having a relatively large probability of originating or transmitting electrical signals which result in arrhythmic activity; and
irradiating the region of cardiac tissue with a radioactive source to create lesions that block electrical conduction in the cardiac tissue.

57. The method of claim 56, wherein locating the region of cardiac tissue includes locating a supraventricular region having a relatively large probability of triggering and contributing to the maintenance of an atrial arrhythmia.

58. The method of claim 57, wherein the supraventricular region is proximate a pulmonary vein.

59. A system for preventing arrhythmia, the system comprising:
a member adapted to locate a region of cardiac tissue having a relatively large probability of originating or transmitting electrical signals which result in arrhythmic activity;
a catheter adapted to be positioned proximate the region of cardiac tissue; and
a radioactive source associated with the catheter for irradiating the region of cardiac tissue to modify electrical conduction of the cardiac tissue.

60. The system of claim 59, wherein the radioactive source is connected to a wire located within a lumen of the catheter.

61. The system of claim 59, wherein the catheter includes an inflatable balloon coupled to the catheter.

62. The system of claim 61, further including a pressurized carbon dioxide gas source for inflating the balloon.

63. The system of claim 61, wherein the inflatable balloon has a predefined shape and where the predefined shape of the balloon defines a geometry of a lesion created by the radioactive source.

64. A system comprising:
   a catheter adapted to be positioned proximate a region of cardiac tissue, wherein the catheter includes an inflatable balloon coupled to the catheter;
   a radioactive source associated with the catheter for irradiating the region of cardiac tissue to create lesions that block electrical conduction in the cardiac tissue; and
   a pressurized carbon dioxide gas source for inflating the balloon.

65. A system comprising:
   a catheter adapted to be positioned proximate a region of cardiac tissue, wherein the catheter includes an inflatable balloon coupled to the catheter; and
   a radioactive associated with the catheter for irradiating the region of cardiac tissue to create lesions that block electrical conduction in the cardiac tissue;
   wherein the inflatable balloon has a predefined shape and where the predefined shape of the balloon defines a geometry of a lesion created by the radioactive source.

66. A system for preventing arrhythmia, the system comprising:
   an elongate flexible catheter having a proximal end and a distal end, where the catheter includes a first lumen extending from a first inlet at the proximal end to a first outlet at the distal end, and a second lumen extending from a second inlet at the proximal end to a second outlet positioned between the proximal and distal ends;
   an inflatable balloon coupled to the elongate flexible catheter, where the flatable balloon at least partially encircles at least a portion of the elongate flexible catheter, and where the inflatable balloon includes an interior surface that defines a chamber in communication with the second outlet of the second lumen;
   a pressurized gas source being releasably coupled to the second inlet of the second lumen and the chamber of the inflatable balloon, where the pressurized gas source inflates the balloon due to gas introduced into the chamber; and
   a wire having a radioactive source positioned on the wire, where the first lumen receives and passes the wire to position the radioactive source adjacent the chamber of the inflatable balloon to allow nuclear energy to pass through the gas in the chamber of the balloon and irradiate tissue in contact with the balloon, wherein the radioactive source is configured to modify electrical conduction of the tissue.

67. The system of claim 66, wherein the inflatable balloon has a shape when inflated that is adapted to contact cardiac tissue of a heart.

68. The system of claim 67, wherein the shape of the inflatable balloon is cylindrical.

69. The system of claim 67, wherein the shape of the inflatable balloon is conical.

70. The system of claim 67, wherein the shape of the inflatable balloon is spherical.

71. The system of claim 67, wherein the shape of the inflatable balloon is spheroidal.

72. The system of claim 67, wherein the shape of the inflatable balloon is adapted to at least partially conform to a pulmonary vein.

73. The system of claim 67, wherein the shape of the inflatable balloon is adapted to at least partially conform to a portion of an atrial chamber.

74. The system of claim 67, wherein the shape of the inflatable balloon is adapted to at least partially conform to a portion of a ventricular chamber.

75. The system of claim 66, wherein the radioactive source is an isotope.

76. The system of claim 66, wherein the chamber of the inflatable balloon includes a central portion and where the wire having the radioactive source positioned on the wire is located in the central portion of the chamber inflatable balloon so as to expose tissue adjacent the inflated balloon to a uniform level of radiation.

77. The system of claim 66, wherein the inflatable balloon has a predefined shape and where the predefined shape of the balloon defines a geometry of a lesion created by the radioactive source.

78. The system of claim 66, wherein the gas of the pressurized gas is carbon dioxide gas.

79. The system of claim 66, wherein the wire includes a distal tip and the radioactive source is positioned on the wire at the distal tip of the wire.

80. The system of claim 66, wherein the radioactive source is positioned along a predetermined portion of the wire.

81. The system of claim 66, wherein the inflatable balloon includes an exterior surface that defines one or more channels adapted to pass blood when the inflatable balloon is inflated.

82. A system for preventing arrhythmia, the system comprising:
   a catheter having a proximal end and a distal end, where the catheter includes a first lumen extending from a first inlet at the proximal end to first outlet at the distal end, the catheter having a predefined shape to position the catheter proximate a cardiac tissue; and
   a radioactive source positioned within the catheter, wherein the radioactive source is configured to modify electrical conduction of the cardiac tissue;
   wherein the radioactive source has a length in a range between approximately 0.5 cm to approximately 4.0 cm.

83. The system of claim 82, wherein the radioactive source has a length of approximately 2.0 cm.

84. A system for preventing arrhythmia, the system comprising:
   a catheter having a proximal end and a distal end, where the catheter includes a first lumen extending from a first inlet at the proximal end to first outlet at the distal end, the catheter having a predefined shape to position the catheter proximate a cardiac tissue; and
   a radioactive source positioned within the catheter, wherein the radioactive source is configured to modify electrical conduction of the cardiac tissue;
   wherein the catheter includes a helical-shaped catheter adapted to fit within a pulmonary vein.

* * * * *

UNITED STATES PATENT AND TRADEMARK OFFICE
CERTIFICATE OF CORRECTION

PATENT NO. : 6,955,640 B2  Page 1 of 1
APPLICATION NO. : 09/967469
DATED : October 18, 2005
INVENTOR(S) : Richard S. Sanders It is certified that error appears in the above-identified patent and that said Letters Patent is hereby corrected as shown below:

On the face page, in field (75), under "Inventors", in column 1, line 1, delete "Woodbury" and insert -- Stillwater --, therefor.

In column 11, line 15, in Claim 4, delete "regulates" and insert -- regulating --, therefor.

In column 11, line 50, in Claim 15, after "probability" insert -- of --.

In column 11, line 59, in Claim 15, delete "a" and insert -- at --, therefor.

In column 14, line 37, in Claim 54, delete "programmed" and insert -- programming --, therefor.

In column 15, line 27, in Claim 65, after "radioactive" insert -- source --.

In column 15, line 42, in Claim 66, delete "flatable" and insert -- inflatable --, therefor.

Signed and Sealed this

Fifth Day of February, 2008

JON W. DUDAS
*Director of the United States Patent and Trademark Office*